United States Patent [19]

Schattschneider

[11] Patent Number: 4,772,851
[45] Date of Patent: Sep. 20, 1988

[54] GENERAL PURPOSE POTENTIOSTATIC TEST SYSTEM USING A MULTIPLEXER FOR TEST ELECTRODE SELECTION

[75] Inventor: George K. Schattschneider, Victoria, Canada

[73] Assignee: Minister of National Defence of Her Majesty's Canadian Government, Ottawa, Canada

[21] Appl. No.: 886,364

[22] Filed: Jul. 17, 1986

[30] Foreign Application Priority Data

Jan. 28, 1986 [CA] Canada .................................. 500508

[51] Int. Cl.⁴ ...................... G01N 27/06; G01N 27/26
[52] U.S. Cl. .................................. 324/425; 324/71.1; 324/71.2; 204/400
[58] Field of Search ..................... 324/425, 71.2, 71.1, 324/65 CR, 453, 456, 348; 204/404, 1 C, 400, 412

[56] References Cited

U.S. PATENT DOCUMENTS

| | | | |
|---|---|---|---|
| 3,855,101 | 12/1974 | Wilson | 204/404 X |
| 4,190,502 | 2/1980 | Kanno et al. | 204/1 C |
| 4,191,920 | 3/1980 | Guttenplan et al. | 324/71.1 X |
| 4,230,554 | 10/1980 | Blanke | 324/425 X |
| 4,506,226 | 3/1985 | Luce et al. | 324/425 X |
| 4,564,422 | 1/1986 | Simoneau et al. | 204/400 X |
| 4,591,792 | 5/1986 | Birchmeier et al. | 324/71.1 X |

FOREIGN PATENT DOCUMENTS 1193659 9/1985 Canada .............................. 324/425

Primary Examiner—Reinhard J. Eisenzopf
Assistant Examiner—Jack B. Harvey
Attorney, Agent, or Firm—Nixon & Vanderhye

[57] ABSTRACT

A general purpose potentiostatic test system, used to provide potentiostatic control of test electrodes using a multiplexer in both the anodic and cathodic regimes. A built-in data switching and measurement subsystem enables rapid and precise determination of the set potentials as well as the test electrode currents. All the test electrodes can be placed in the same test tank and use a single auxiliary electrode.

11 Claims, 3 Drawing Sheets

GENERAL PURPOSE POTENTIOSTATIC TEST SYSTEM USING A MULTIPLEXER FOR TEST ELECTRODE SELECTION

FIELD OF THE INVENTION

This invention relates to current-measuring instruments for multiple-potential, multiple-electrode potentiostatic testing and more particularly to instruments which enable bipolar potentiostatic testing of a large number of test electrodes at several different set potentials in a single test tank.

BACKGROUND AND SUMMARY OF THE INVENTION

Corrosion scientists have often found the need to perform concurrent testing of large numbers of materials, at a variety of set potentials, all within a common test tank. A system was therefore required to provide the potentiostatic control functions and the high accuracy measurement capabilities required to fulfill many of todays corrosion testing needs.

The potentiostat is an instrument that automatically varies the current flow between a test electrode and an auxiliary electrode in order to regulate the potential between the test electrode and a reference electrode.

In a typical three-electrode potentiostatic circuit, the potentiostat has two inputs and one output. The inputs are potentials from the reference electrode and a user-adjusted set potential. The reference electrode is buffered so that negligible current flows through it. The potentiostat causes the potential between the reference electrode and the test electrode to equal the set potential by controlling the current flowing between the auxiliary electrode and test electrode. The value of the current is determined by some non-intrusive method of current measurement. Commercial corrosion test systems, such as the Princeton Applied Research Model 350A, are capable of very accurately controlling and measuring potentiostatic reactions over an extremely wide range of potentials and currents. However, the systems are quite expensive and are only capable of controlling a single three-electrode system at one time.

Another requirement of corrosion scientists was the need to perform concurrent testing of the cathodic properties of a large number of materials at several different potentials. The same test tank was to be used to ensure that all materials experience the same electrolytic conditions. Since a single test could considerably run for months or even years, it was uneconomical to use commercial three-electrode test systems to test a large number of materials. Therefore, a multiple-test electrode, multiple-set-potential instrument, dubbed the Long-Term Current Demand Control System, was designed and built to fulfill the cathodic research requirements of corrosion scientists. Such a control system is disclosed and claimed in Canadian Pat. No. 1,193,659 issued Sept. 17, 1985 in the name of Her Majesty the Queen in Right of Canada as represented by the Minister of National Defence.

Another need which has arisen for corrosion scientists is to perform corrosion studies on the anodic side of the polarization characteristics of several materials. It is in this region that pitting and crevice corrosion takes place. A practical use of this knowledge is in the consideration of possible materials for undersea applications. An example might be the examination of new alloys for use in the construction of variable-depth sonar cables. Anodic protection is also used quite widely in industry; e.g. to inhibit corrosion in the chemical vats used at pulp and paper mills.

Although it may appear that the determination of the polarization characteristics of materials should not be difficult, there is an induction time during which, for any given set potential, the material must undergo a transient chemical reaction before settling down to its steady-state condition. A material may require an induction time of days or even weeks before its ultimate current value is reached. Furthermore, because of the manner in which pits and crevices form in corroding materials, most of the change in the magnitude of the current flow might take place in the last few hours or days of the test. Therefore, accurately establishing the polarization curve of a single material could require months of testing if a reasonable number of points are measured and if only a single potentiostat is available.

To resolve the problem would require the use of a bank of potentiostats controlling a group of identical test specimens, with each potentiostat determining a single point on the material's polarization curve. As indicated earlier, it would be economically unreasonable to use a large number of commercial potentiostats to perform such testing. Therefore, it was recognized that there was a distinct need for an anodic or positive-potential potentiostatic control system.

As a result, the General Purpose Potentiostatic Test System (GPPTS), which is the subject of this invention was designed. The GPPTS is an electronic instrument which is capable of potentiostatically controlling a large number of test electrodes at several different set potentials on both the anodic and cathodic sides of their polarization characteristics.

For example, the GPPTS can control up to 56 test electrodes, in groups of seven, at up to eight different set potentials. The set potentials can be adjusted to any value between ±2.0 volts with respect to a reference electrode. Furthermore, the entire test can be performed within a single large test tank using a single auxiliary electrode. The GPPTS is provided with a built-in measurement system which can accurately determine the impressed current at any test electrode and display it with $3\frac{1}{2}$ digits of resolution.

In the new design, the auxiliary electrode is grounded and the test electrode is directly controlled by the potentiostat.

The current measurement takes place at the test electrode. In a single-test-electrode system, the current measurement could also take place at the auxiliary electrode. However, since it is desired to extend the design to a multiple-test-electrode—single-auxiliary-electrode system, it is necessary to make the measurement at the test electrode.

It is therefore an object of the present invention to provide a bipolar potentiostatic test system which is capable of potentiostatically controlling a large number of test electrodes at several different set potentials on both the anodic and cathodic sides of their polarization characteristics.

Another object of the present invention is to provide a bipolar potentiostatic test system having a switching and measurement system which will enable the rapid and precise determination of set potentials as well as any individual test electrode current.

Yet another object of the present invention is to provide a bipolar potentiostatic test system in which all test electrodes are placed in the same test tank and will draw current directly from the same auxiliary electrode.

According to one aspect of the invention, there is provided an apparatus to provide bipolar potentiostatic control of test electrodes, said test electrodes forming part of an electrical potentiostatic circuit having an auxiliary electrode and reference electrode wherein said electrodes are immersed in an electrolyte, comprising potential supply means for providing an adjustable set potential to said potentiostatic circuit; buffer means connected to said reference electrode to provide a buffered signal; adding means for adding said set potential and said buffered signal to obtain a computed potential; driver means for maintaining said test electrodes at said computed potential by controlling the current flow between said test electrodes and said auxiliary electrode; measuring means to determine the value of said adjustable set potential and said current flow wherein a variation of said current flow is indicative of corrosion action affecting said test electrodes; display means for displaying said computed potential and said current flowing through said test electrodes.

According to a second aspect of the invention, there is provided, a method of providing bipolar potentiostatic control of test electrodes, said test electrodes forming part of an electrical potentiostatic circuit having an auxiliary electrode and reference electrode wherein said electrodes are immersed in an electrolyte, comprising the steps of applying an adjustable set potential to said potentiostatic circuit; buffering the output of said reference electrode to provide a buffered signal; adding said set potential and said buffered signal to obtain a computed potential; maintaining, by driver means, said test electrodes at said computed potential by controlling the current flow between said test electrodes and said auxiliary electrode; measuring the value of said adjustable set potential and said current flowing through said test electrodes wherein a variation of said current flow is indicative of corrosion action affecting said test electrodes; displaying said adjustable set potential and said current flowing through said test electrodes.

BRIEF DESCRIPTION OF THE DRAWINGS

These and other features and advantages of this invention will become apparent from the detailed description below. That description is to be read in conjunction with the accompanying drawings in which.

DETAILED DESCRIPTION

Figure 1:
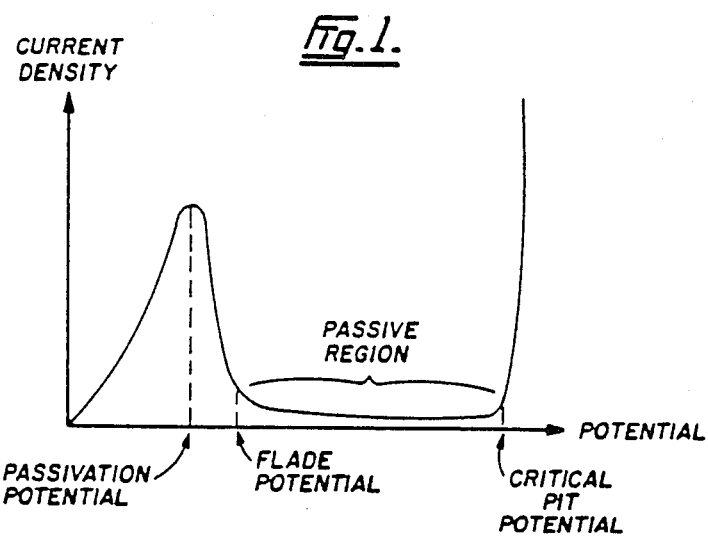
FIG. 1 is a graph showing a typical anodic polarization curve.

Referring now to FIG. 1, illustrated is the E-I relationship that is typical of materials operating in the anodic regime. If the test material is maintained at a potential within the passive region, corrosion will be inhibited. If the potential falls below the Flade potential, some corrosion will take place. If the critical pit potential is exceeded, the material will corrode very rapidly. This is why it is essential to know the precise values of all these potentials.

Figure 2:
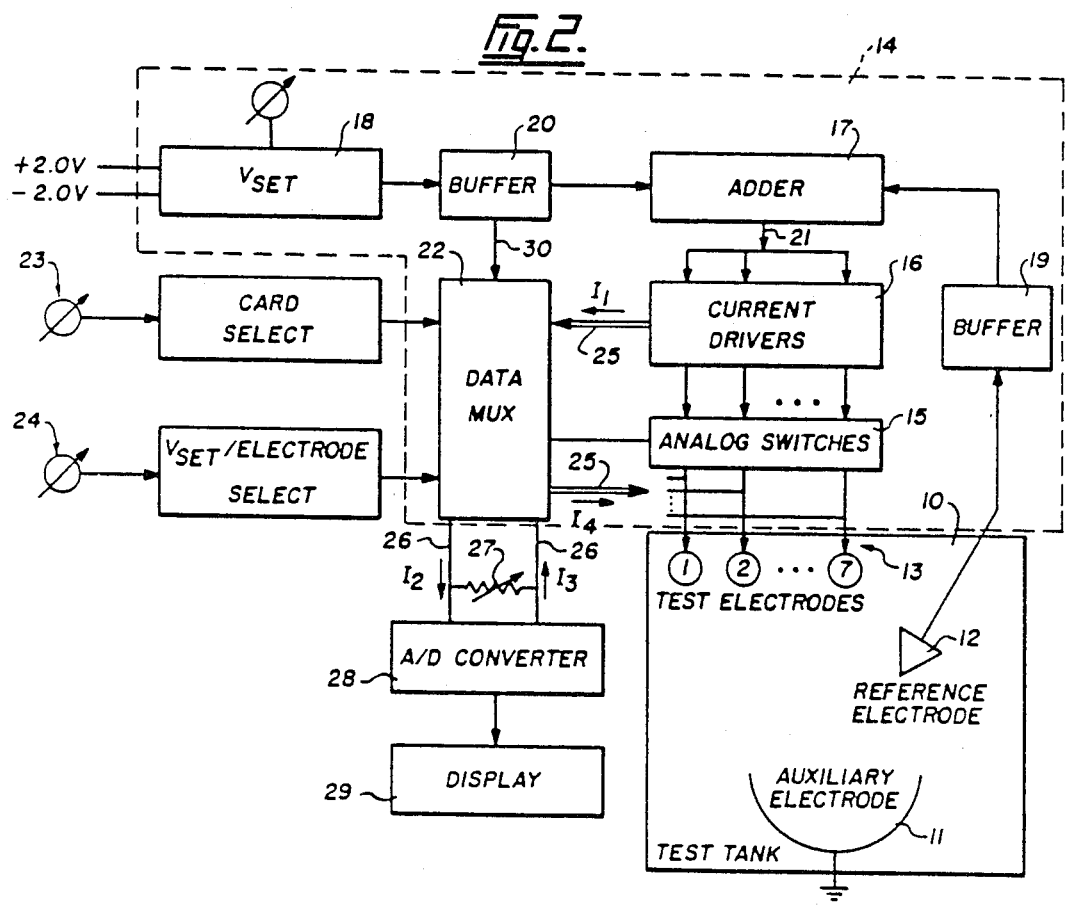
FIG. 2 is a block diagram of the bipolar potentiostatic system according to the present invention.

In a typical potentiostatic test system, there could be eight potentiostatic cards, and each card could control up to seven test electrodes at some operator adjusted set potential between plus and minus 2 volts. FIG. 2 is a block diagram of the bipolar potentiostatic system using a single potentiostatic card. The bipolar potentiostatic system of FIG. 2 consists of a test tank 10 into which is immersed an auxiliary electrode 11 connected to ground, a reference electrode 12 and a number of test electrodes 13. This bank of electrodes 13 will be tested at a single set potential. These test electrodes are connected to one potentiostatic card 14 which is comprised of analog switches 15 current drivers 16, adder 17, adjustable set potential 18, buffers 19 and 20, and data multiplexer 22. A number of additional potentiostatic cards each controlling a number of test electrodes could be added to the circuit shown in FIG. 2. Each potentiostatic card and associated test electrodes could be maintained at a separate set potential between plus 2 volts and minus 2 volts. The output potentials from the reference electrode 12 and adjustable set potential 18 are buffered by buffers 19 and 20 respectively. As is shown the outputs of the reference electrode buffer 19 and the adjustable set potential buffer 20 are added together by adder 17 to produce the value of the potential 21 at which the test electrodes 13 must be maintained. The current drivers 16 then maintain the test electrodes 13 at this computed potential by inducing the necessary current flow in the appropriate polarity. The data multiplexer circuitry 22 enables rapid and precise determination of the adjustable set potential 30 as well as the test-electrode currents.

In operation, the operator-controlled cardselect switch 23 sends out the information to the data-multiplexer circuitry 22 to enable the selection of one out of eight of the potentiostatic cards 14. Then, the operator-controlled $V_{set}$/electrode select switch 24 sends out the information to the data multiplexer circuitry 22 to enable the selection of either the $V_{set}$ value or, as in this example, one of the seven test currents of the test electrodes 13 controlled by the selected card 14. The data multiplexer circuitry 22 and associated logic (not shown) will then perform the necessary switching of analog switches 15 to divert the selected test-electrode current out to the measuring data bus 25. As indicated in FIG. 2 by currents I1, I2, I3 and I4, current I1 will then flow through bus 25 from current drivers 16, down bus 26 (I2), through a high precision resistor 27, back up bus 26 (I3), and out through bus 25 (I4) to the test electrode. A high accuracy A-to-D converter 28 measures the voltage across the precision resistor 27 and thereby indirectly measures the test-electrode current. Finally, the value of the test-electrode current is displayed on a $3\frac{1}{2}$ digit front-panel readout 29.

Figure 3:
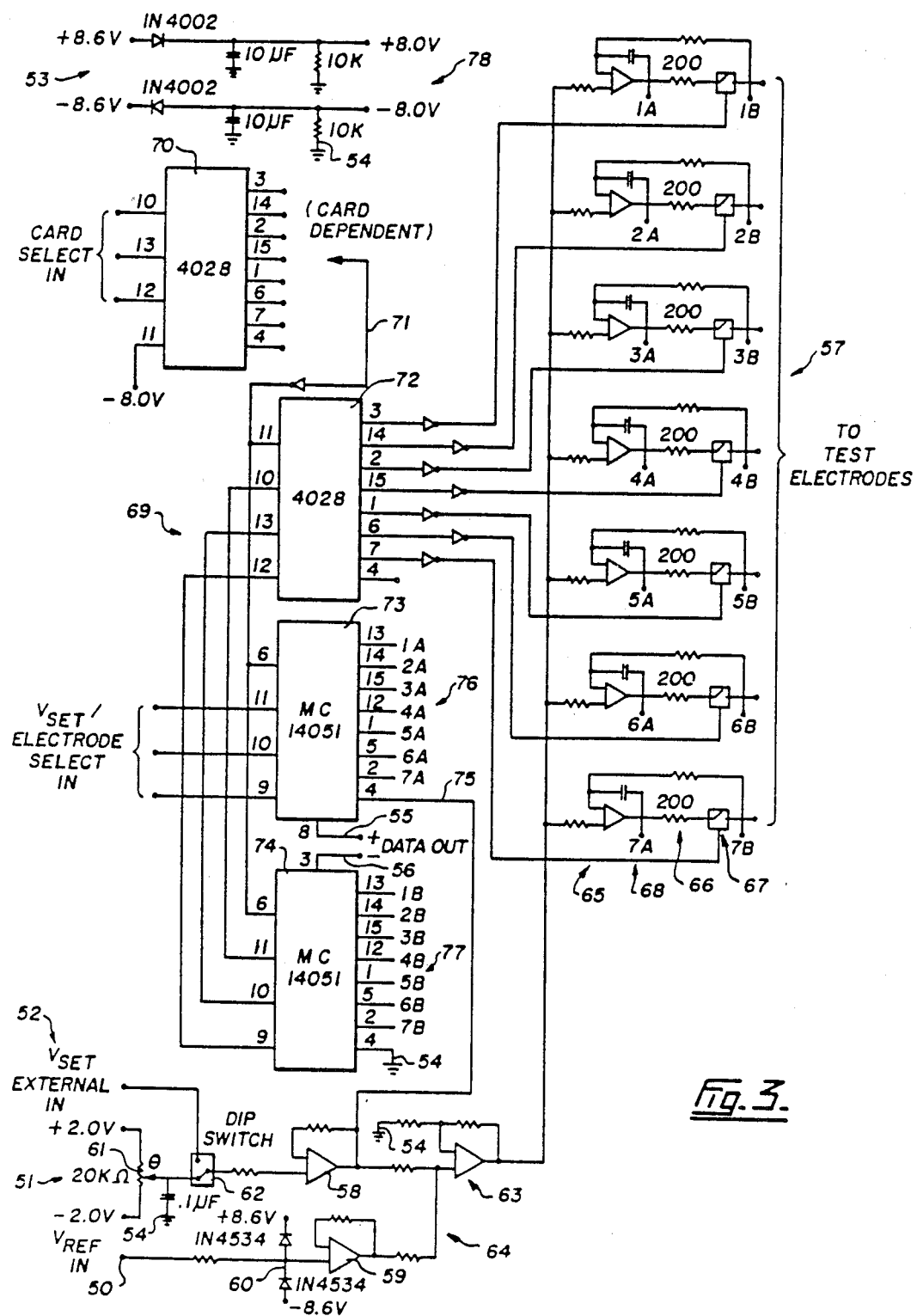
FIG. 3 is a schematic diagram of a single potentiostatic card forming part of the present invention.

The electronic realization of the potentiostatic card design concept described earlier is shown in schematic form in FIG. 3. The circuit has thirteen inputs and nine outputs. Seven of the inputs are linear and six are digital. Of the six digital inputs, three are the card select inputs and three are the $V_{set}$/electrode select inputs. The seven linear inputs are: $V_{ref.in}$ at 50, ±2.0V at 51, $V_{set.ext.in}$ at 52, ±8.6V at 53, and ground at 54. $V_{ref.in}$ 50 is the input terminal for the reference electrode corresponding to that particular card. The ±2 volt inputs 51 provide a regulated voltage source for the on-card adjustable set potential. The $V_{set.ext.in}$ terminal 52 provides for the application of an externally generated set potential. The ±8.6 volt input 53 supplies power to the circuitry on the card. Finally, the ground terminals 54 act as a power return as well as a zero volt reference point.

Of the nine output terminals, two provide the card's connection to the system's measurement data bus as shown at 55 and 56. The other seven outputs 57 provide the connections from the potentiostatic outputs to their corresponding test electrodes. All of the op amps used in the circuit are uA714s. These are precision op amps with the characteristics of low noise, low drift, and very low input-offset voltage. With power supply voltages of ±8.6 volts, the op amp current consumption is less than 2 milli-amps each.

Two of the 714s 58 and 59 are configured as voltage followers to act as buffers for the reference electrodes $V_{ref.in}$ 50 and the set potential 51. The $V_{ref.in}$ input has protection diodes 60 to guard against input voltages greater than ±8.6 volts. The set potential 51 is operator-adjusted between ±2 volts with a multiturn trim pot 61. There is also a single-pole double-throw DIP switch 62 provided to permit the application of an external set potential 52. The outputs of the two voltage followers are combined in a unitygain adder circuit 63 to determine the potential at which the test electrodes must be maintained. The resistors that are used in the three-op-amp subcircuit 64 are taken from a Beckman precision resistor array. The resistors in the array are specified to match each other to within at least 0.1%. This ensures that an extremely high accuracy addition is performed. The output of the adder circuit 63 is applied to the inputs of current drivers, as indicated by the group of op amps 65, that control the test electrodes. These op amps provide whatever current is necessary, up to ±10 mA each, to maintain the test electrodes at the desired potential. Each of these op amps has a 200 ohm resistor 66 and an analog switch 67 lying between its output and its corresponding testelectrode terminal. These components do not affect the accuracy of the op amps' control of the potential of the test electrodes. This remains true as long as the sensing point for the inverting input of the op amp is connected to the test electrode and a feedback capacitor 68 is included to maintain stability.

Figure 4:
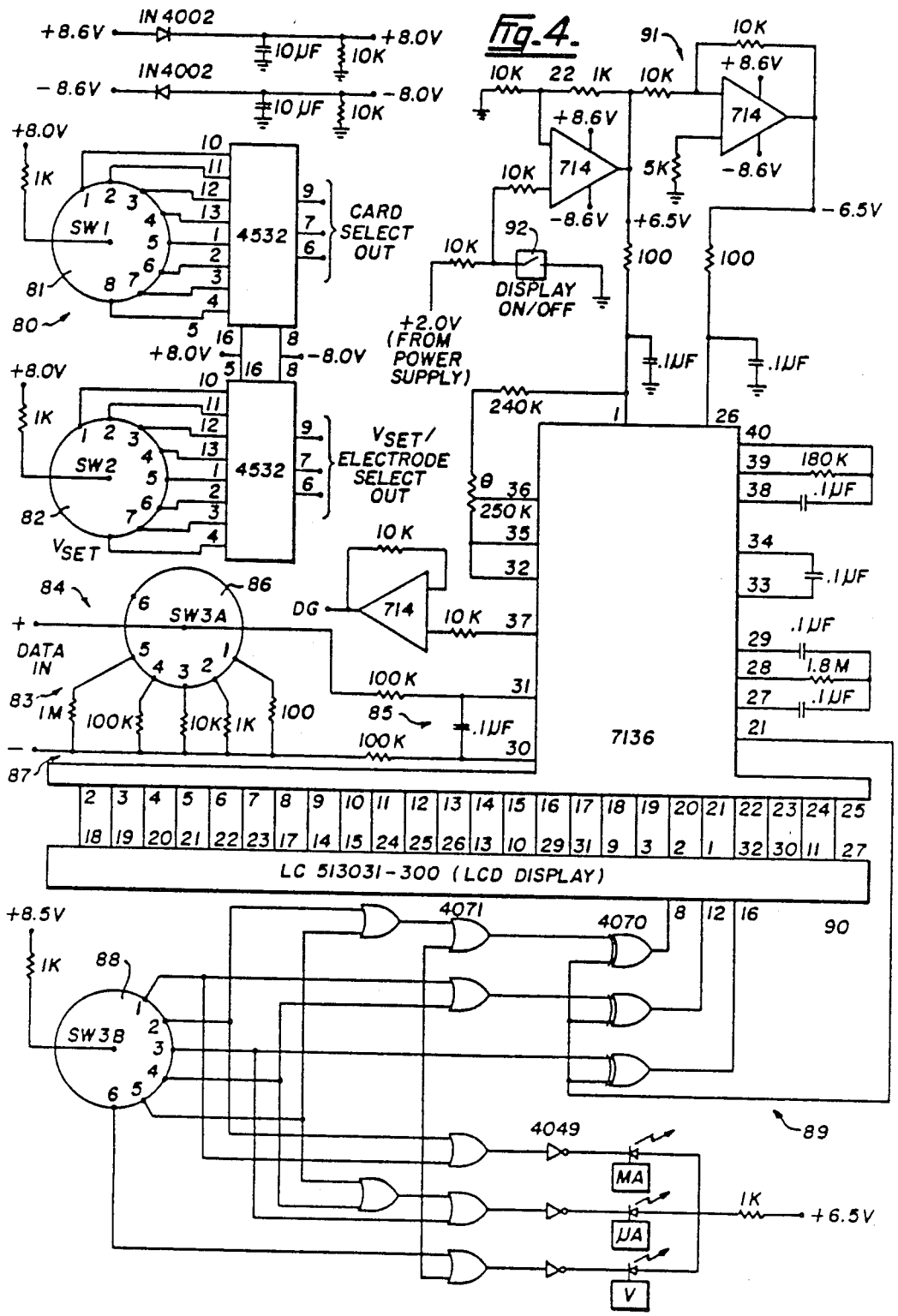
FIG. 4 is a schematic diagram of the measurement circuit used in the present invention.

FIG. 4 shows a schematic diagram of the measurement sub-system. Communication between the dataselect circuit 69 shown in FIG. 3 and the measurement sub-system circuit shown in FIG. 4 takes place over a six-wire digital address bus and a two-wire analog data bus. The circuitry shown at 80 produces six address bits. Of the six address bits, three provide card-select information and three provide the desired-data-select information. The three card-select bits provide a means to choose any one of the eight potentiostatic cards. The other three bits choose either the set potential or one of the seven test-electrode currents as the data to be sent from the selected card to the two-wire analog data bus. As the operator adjusts switches 81 and 82, the normally low 4532 input lines that correspond to the selected card and the desired analog data are pulled high. Each of the 4532s then produces a three-bit digital signal that corresponds to the activated input. Finally, the six-bit address is placed onto the digital address bus.

If we now refer back to FIG. 3, the three card-select bits are fed into a 4028 shown at 70. The 4028 converts the three-bit binary input to a one-of-eight output signal. Each of the eight potentiostatic cards has its data multiplexer activation line 71 connected to a different one of the eight outputs of the 4028, 70. When a specific card is selected and the appropriate 4028 output goes high, a second 4028, shown at 72 and two 14051s shown at 73 and 74 are activated. A 14051 is an eight-to-one analog multiplexer. Based on the other three address bits, either the card's set potential or one of the seven test-electrode currents is selected as data to be measured. If the set potential is selected, the two corresponding 14051 inputs are connected to the output 75 of the $V_{set}$ buffer 58 and to ground. As shown, the 14051 outputs are directly connected to the measurement data bus 55 and 56. The second 4028, at 70 is not used in this case. If, however, one of the test-electrode currents is selected, then the second 4028, at 70, opens the analog switch 67 that directly passes the current from the op-amp 65 to the selected test electrode 57. At the same time, the appropriate analog switches within the 14051's are closed to connect the op-amp output 76 to one of the data lines and the test-electrode terminal 77 to the other data line. It should be noted at this point that the supply voltages for the CMOS integrated circuits are ±8 volts. The ±8 volts is derived by inserting a silicone diode in series with each of the ±8.6 volt lines as shown at 78. The 16 volt CMOS supply minimizes the analog switch "on resistance" and maximizes the signal amplitude handling range. Furthermore, the supply voltage is still safely within the maximum 18 volts permitted for these integrated circuits.

Returning now to FIG. 4, we find that the two data inputs 83 are connected to the differential inputs of the 7136, a low power 3½ digit A/D converter, at pins 30 and 31 through a switching network 84 and a balanced low-pass filter 85. For set-potential measurements, switch 86 is set to position 6. For current measurements, the switch is positioned to the appropriate resistor for the current range being measured. The full scale input to the 7136 converter is ±2 volts. Therefore, if, for example, the measured current is somewhere between 20 micro-amps and 200 micro-amps, then the switch would be positioned to the 10 kohm resistor. The 10 kohm value is determined by dividing the fullscale voltage 2 volts by the full scale current 200 micro-amps. The five current-measuring resistors are selected to an accuracy of better than 0.1%. As shown, at 87, they are selected to cover the current range from 2 micro-amps to 20 milli-amps full scale in one decade steps. Although the measurement circuit will work accurately up to 20 milli-amps, the entire system is only designed to work up to 10 milli-amps. This is due to production variations in the maximum output-current capabilities of the op amps as well as the on resistances of the analog switches used on the potentiostatic cards. Switch 88 is the second deck of switch 86. Therefore, when the switch is adjusted, both 86 and 88 move together. Switch 88 is connected to a group of OR gates 89 to turn on the appropriate decimal point and annunciators on the front panel display 90. If the switch is in position 1, the format of the readout will be X.XXX micro-amp. Similarly, position 2 produces XX.XX microamp, position 3 produces XXX.X micro-amp, position 4 produces X.XXX milli-amp, position 5 produces XX.XX milli-amp, and position 6 produces X.XXX V. The actual measurement is performed by the 7136 A/D converter. The 7136, which operates at three conversion per second, is both inexpensive and extremely accurate. The two op amps 91 in the measurement circuit provide a ±6.5 volt power source for the 7136. An on-off switch 92 for the 7136 is also provided. Finally, as shown in FIG. 4, the 7136 drives a 3½ digit LCD display 90 without any additional interfacing circuitry.

The embodiments of the invention in which an exclusive property or privilege is claimed are defined as follows:

1. An apparatus to provide bipolar potentiostatic control of test electrodes, said test electrodes forming part of an electrical potentiostatic circuit having an auxiliary electrode and reference electrode wherein said electrodes are immersed in an electrolyte, comprising:
    potential supply means for providing an adjustable set potential to said potentiostatic circuit;
    buffer means connected to said reference electrode and said potential supply means to provide a first and second buffered signal;
    adding means for adding said first and second buffered signals to obtain a computed potential;
    driver means for maintaining said test electrodes at said computed potential by controlling the current flow between said test electrodes and said auxiliary electrode;
    measuring means to determine the value of said adjustable set potential and said current flow wherein the value of said current flowing is indicative of the corrosive action affecting said test electrodes,
    said measuring means including multiplexer means coupled to said driver means for selecting a test electrode to be tested and for sampling the current flowing to said selected test electrode and means for directing the sampled test electrode current to said selected test electrode; and
    display means for displaying said adjustable set potential and said current flowing through said test electrodes.

2. An apparatus as defined in claim 1 wherein said driver means is comprised of operational amplifiers connected to said test electrodes.

3. An apparatus as defined in claim 1 wherein said measuring means includes a current-measuring means coupled to said multiplexer means.

4. Apparatus according to claim 1, wherein at least said driver means, said measuring means and said test electrodes are connected in a closed-loop configuration.

5. Apparatus according to claim 1, wherein said measuring means includes current-measuring means, and said multiplexer means includes means for directing current from said driver means through said current measuring means and to said selected test electrode, whereby the current being measured is the current that is performing the potentiostatic control function.

6. Apparatus according to claim 1, wherein said measuring means includes common current measuring means and wherein said multiplexer means includes means for permitting the current flow to each of a plurality of test electrodes to be measured by said common current measuring means.

7. Apparatus according to claim 1, wherein said supply means, buffer means, adding means, driving means and multiplexer means are fabricated on a potentiostatic card.

8. Apparatus according to claim 7 further including a plurality of potentiostatic cards.

9. A method of providing bipolar potentiostatic control of test electrodes, said test electrodes forming part of an electrical potentiostatic circuit having an auxiliary electrode and reference electrode wherein said electrodes are immersed in an electrolyte, comprising the steps of:
    applying an adjustable set potential to said potentiostatic circuit;
    buffering the output of said reference electrode to provide a buffered signal;
    adding said set potential and said buffered signal to obtain a computed potential;
    maintaining, by driver means, said test electrodes at said computed potential by controlling the currents flowing between said test electrodes and said auxiliary electrode;
    measuring the value of said adjustable set potential and said currents flowing through said test electrodes wherein the values of said currents are indicative of corrosion action affecting said test electrodes;
    said measuring step including the steps of selecting, by multiplexer means, a test electrode to be tested, sampling the current flow to said selected test electrode, and directing the sampled test electrode current to said selected test electrode; and
    displaying said adjustable set potential and said currents flowing through said test electrodes.

10. A method according to claim 9, wherein said measuring step includes the step of directing current from said driver means through a current measuring means and to said selected test electrode, whereby the current being measured is the current that is performing the potentiostatic control function.

11. A method according to claim 9, wherein said measuring step includes the step of measuring the current flow through each of a plurality of test electrodes through a common current measuring means.

* * * * *